(12) United States Patent
Bergheim et al.

(10) Patent No.: US 9,775,704 B2
(45) Date of Patent: Oct. 3, 2017

(54) IMPLANTABLE VALVE PROSTHESIS

(75) Inventors: Bjarne Bergheim, Laguna Hills, CA (US); Keith E. Myers, Lake Forest, CA (US); Jeffrey P. DuMontelle, Irvine, CA (US); Christine Nguyen, Garden Grove, CA (US)

(73) Assignee: Medtronic3F Therapeutics, Inc., Irvine, CA (US)

(*) Notice: Subject to any disclaimer, the term of this patent is extended or adjusted under 35 U.S.C. 154(b) by 2004 days.

(21) Appl. No.: 11/685,025

(22) Filed: Mar. 12, 2007

(65) Prior Publication Data

US 2007/0270944 A1 Nov. 22, 2007

Related U.S. Application Data

(63) Continuation of application No. 11/112,757, filed on Apr. 22, 2005, now abandoned.

(60) Provisional application No. 60/565,118, filed on Apr. 23, 2004.

(51) Int. Cl.
*A61F 2/24* (2006.01)

(52) U.S. Cl.
CPC .......... *A61F 2/2418* (2013.01); *A61F 2/2409* (2013.01); *A61F 2220/0041* (2013.01); *A61F 2220/0075* (2013.01); *A61F 2230/0054* (2013.01)

(58) Field of Classification Search
CPC .... A61F 2/2418; A61F 2/2409; A61F 2/2412; A61F 2/24; A61F 2250/0039; A61F 2250/0018; A61F 2250/0098; Y10S 623/90

USPC .......... 623/1.17, 1.24, 1.26, 2.14, 2.17, 900, 623/2.38, 2.4, 2.41

See application file for complete search history.

(56) References Cited

U.S. PATENT DOCUMENTS

| | | | |
|---|---|---|---|
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |

(Continued)

FOREIGN PATENT DOCUMENTS

| | | |
|---|---|---|
| CN | 2007-100074433 | 8/2007 |
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Brian Pellegrino

(57) ABSTRACT

The present invention provides valve prostheses adapted to be initially crimped in a narrow configuration suitable for catheterization through body ducts to a target location and adapted to be deployed by exerting substantially radial forces from within by means of a deployment device to a deployed state in the target location.

64 Claims, 13 Drawing Sheets

(56) References Cited

U.S. PATENT DOCUMENTS

| | | |
|---|---|---|
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,258,023 A | 11/1993 | Reger |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,800,527 A * | 9/1998 | Jansen et al. ............... 623/2.38 |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,283,127 B1 | 9/2001 | Sterman |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |

(56) References Cited

U.S. PATENT DOCUMENTS

| | | |
|---|---|---|
| 6,425,916 B1 | 7/2002 | Garrison et al. |
| 6,440,164 B1 | 8/2002 | DiMatteo et al. |
| 6,454,799 B1 * | 9/2002 | Schreck .................. 623/2.17 |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,478,806 B2 | 11/2002 | McFarlane |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,063 B1 | 9/2003 | Hunsberger |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu |
| 6,682,559 B2 | 1/2004 | Myers |
| 6,685,724 B1 | 2/2004 | Haluck |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,787 B2 | 4/2004 | Cox |
| 6,719,788 B2 | 4/2004 | Cox |
| 6,719,789 B2 | 4/2004 | Cox |
| 6,730,118 B2 | 5/2004 | Spenser |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |

(56) References Cited

U.S. PATENT DOCUMENTS

| | | |
|---|---|---|
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225356 A1* | 11/2004 | Frater .......................... 623/2.14 |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |

(56) References Cited

U.S. PATENT DOCUMENTS

| | | |
|---|---|---|
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0234940 A1 | 9/2010 | Dolan |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 A | 3/1981 |
| GB | 2433700 | 12/2007 |
| SU | 1271508 | 11/1986 |
| WO | 95/29640 | 11/1995 |
| WO | WO 00-12032 A1 | 3/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | WO 02-49546 A2 | 6/2002 |
| WO | 03/003943 | 1/2003 |
| WO | 03/003949 | 1/2003 |
| WO | 03/011195 | 2/2003 |
| WO | WO 03-047468 A1 | 6/2003 |
| WO | 2004/019825 | 3/2004 |
| WO | 2004/089250 | 10/2004 |
| WO | 2005/004753 | 1/2005 |
| WO | WO 2005-046528 | 5/2005 |
| WO | 2006/026371 | 3/2006 |

(56) References Cited

FOREIGN PATENT DOCUMENTS

| WO | 2008/047354 | 4/2008 |
|---|---|---|
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," in: Topol EJ, ed. Textbook of Interventional Cardiology. Volume II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. HC 08C00934 (83 pages).
Expert report of Dr. Nigel Buller, non-confidential annex—infringement, dated Jan. 12, 2009, Edwards' United Kingdom action for invalidity, Claim No. HC 08C00934 (12 pages).
Expert report of Dr. Rodolfo Quijano, dated Jan. 9, 2009, Edwards' United Kingdom action for invalidity, Claim No. HC 08C00934 (18 pages).
First Expert report of Prof. David Williams, dated Jan. 12, 2009, Edwards' United Kingdom action for invalidity, Claim No. HC 08C00934 (41 pages).

(56) References Cited

OTHER PUBLICATIONS

First Expert report of Prof. Martin Rothman, dated Jan. 12, 2009, *Edwards Lifesciences and Cook Biotech*, Edwards' United Kingdom action for invalidity, Claim No. HC 08CO0934 (64 pages).
Fourth Expert report of Prof. Martin Rothman, dated Apr. 22, 2009, *Edwards Lifesciences and Cook Biotech*, Edwards' United Kingdom action for invalidity, Claim No. HC 08CO0934 (10 pages).
Second Expert report of Dr. Nigel Buller, dated Feb. 25, 2009, Edwards' United Kingdom action for invalidity, Claim No. HC 08CO0934 (24 pages).
Second Expert report of Dr. Rodolfo Quijano, dated Feb. 26, 2009, Edwards' United Kingdom action for invalidity, Claim No. HC 08CO0934 (6 pages).
Second Expert report of Prof. David Williams, dated Feb. 5, 2009, Edwards' United Kingdom action for invalidity, Claim No. HC 08CO0934 (15 pages).
Second Expert report of Prof. Martin Rothman, dated Feb. 5, 2009, *Edwards Lifesciences and Cook Biotech*, Edwards' United Kingdom action for invalidity, Claim No. HC 08CO0934 (11 pages).
Third Expert report of Dr. Nigel Buller, dated Apr. 21, 2009, Edwards' United Kingdom action for invalidity, Claim No. HC 08CO0934 (6 pages).
Third Expert report of Dr. Rudolfo Quijano, dated Apr. 27, 2009, Edwards' United Kingdom action for invalidity, Claim No. HC 08CO0934 (3 pages).
Third Expert report of Prof. David Williams, dated Apr. 22, 2009, Edwards' United Kingdom action for invalidity, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe (3 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Expert Rebuttal Report of Prof. Martin T. Rothman (32 pages) redacted, *Edwards* v. *Core Valve*, U.S. District Court, District of Delaware, Case No. 08-091, dated Jul. 29, 2009.
Expert Report of Prof. Martin T. Rothman (74 pages) redacted, *Edwards* v. *CoreValve*, U.S. District Court, District of Delaware, Case No. 08-091, dated Jun. 29, 2009.
First Expert report of Richard A. Hillstead (41 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

\* cited by examiner

IMPLANTABLE VALVE PROSTHESIS

CROSS REFERENCE TO RELATED APPLICATIONS

This application is a continuation of U.S. patent application Ser. No. 11/112,757, filed Apr. 22, 2005, which claims the benefit of U.S. Provisional Application No. 60/565,118, filed Apr. 23, 2004, the entireties of which are hereby incorporated by reference

FIELD OF THE INVENTION

The present invention relates to implantable devices. More specifically, the present invention relates to heart valve prosthetic devices for cardiac implantation. The present invention may also be utilized in other body cavities, vessels, or ducts.

BACKGROUND OF THE INVENTION

The transport of vital fluids in the human body is largely regulated by valves. Physiological valves are designed to prevent the backflow of bodily fluids, such as blood, lymph, urine, bile, etc., thereby keeping the body's fluid dynamics unidirectional for proper homeostasis. For example, venous valves maintain the upward flow of blood, particularly from the lower extremities, back toward the heart, while lymphatic valves prevent the backflow of lymph within the lymph vessels, particularly those of the limbs.

Because of their common function, valves share certain anatomical features despite variations in relative size. The cardiac valves are among the largest valves in the body with diameters that may exceed 30 mm, while valves of the smaller veins may have diameters no larger than a fraction of a millimeter. Regardless of their size, however, many physiological valves are situated in specialized anatomical structures known as sinuses. Valve sinuses can be described as dilations or bulges in the vessel wall that houses the valve. The geometry of the sinus has a function in the operation and fluid dynamics of the valve. One function is to guide fluid flow so as to create eddy currents that prevent the valve leaflets from adhering to the wall of the vessel at the peak of flow velocity, such as during systole. Another function of the sinus geometry is to generate currents that facilitate the precise closing of the leaflets at the beginning of backflow pressure. The sinus geometry is also important in reducing the stress exerted by differential fluid flow pressure on the valve leaflets or cusps as they open and close.

Thus, for example, the eddy currents occurring within the sinuses of Valsalva in the natural aortic root have been shown to be important in creating smooth, gradual and gentle closure of the aortic valve at the end of systole. Blood is permitted to travel along the curved contour of the sinus and onto the valve leaflets to effect their closure, thereby reducing the pressure that would otherwise be exerted by direct fluid flow onto the valve leaflets. The sinuses of Valsalva also contain the coronary ostia, which are outflow openings of the arteries that feed the heart muscle. When valve sinuses contain such outflow openings, they serve the additional purpose of providing blood flow to such vessels throughout the cardiac cycle.

When valves exhibit abnormal anatomy and function as a result of valve disease or injury, the unidirectional flow of the physiological fluid they are designed to regulate is disrupted, resulting in increased hydrostatic pressure. For example, venous valvular dysfunction leads to blood flowing back and pooling in the lower legs, resulting in pain, swelling and edema, changes in skin color, and skin ulcerations that can be extremely difficult to treat. Lymphatic valve insufficiency can result in lymphedema with tissue fibrosis and gross distention of the affected body part. Cardiac valvular disease may lead to pulmonary hypertension and edema, atrial fibrillation, and right heart failure in the case of mitral and tricuspid valve stenosis; or pulmonary congestion, left ventricular contractile impairment and congestive heart failure in the case of mitral regurgitation and aortic stenosis. Regardless of their etiology, all valvular diseases result in either stenosis, in which the valve does not open properly, impeding fluid flow across it and causing a rise in fluid pressure, or insufficiency/regurgitation, in which the valve does not close properly and the fluid leaks back across the valve, creating backflow. Some valves are afflicted with both stenosis and insufficiency, in which case the valve neither opens fully nor closes completely.

Because of the potential severity of the clinical consequences of valve disease, valve replacement surgery is becoming a widely used medical procedure, described and illustrated in numerous books and articles. When replacement of a valve is necessary, the diseased or abnormal valve is typically cut out and replaced with either a mechanical or tissue valve. A conventional heart valve replacement surgery involves accessing the heart in a patient's thoracic cavity through a longitudinal incision in the chest. For example, a median sternotomy requires cutting through the sternum and forcing the two opposite halves of the rib cage to be spread apart, allowing access to the thoracic cavity and the heart within. The patient is then placed on cardiopulmonary bypass, which involves stopping the heart to permit access to the internal chambers. Such open heart surgery is particularly invasive and involves a lengthy and difficult recovery period. Reducing or eliminating the time a patient spends in surgery is thus a goal of foremost clinical priority.

One strategy for reducing the time spent in surgery is to eliminate or reduce the need for suturing a replacement valve into position. Toward this end, valve assemblies that allow implantation with minimal or no sutures would be greatly advantageous. Attaching a valve such as a tissue valve to a support structure such as a stent may enable a valve assembly that allows implantation with minimal or no sutures. It is important that such valve constructs are configured such that the tissue leaflets or the support valve don't come into contact with the support structure, either during the collapsed or expanded state, or both in order to prevent abrasion. Such contact is capable of contributing undesired stress on the valve leaflet. Moreover, it is advantageous that such support structures are configured to properly support a tissue valve having a scalloped inflow annulus such as that disclosed in the U.S. patent application Ser. No. 09/772,526, issued as U.S. Pat. No. 6,682,559 on Jan. 27, 2004, which is incorporated by reference herein in its entirety.

Accordingly, there is a need for a valve replacement system comprising a collapsible and expandable valve assembly that is capable of being secured into position with minimal or no suturing; facilitating an anatomically optimal position of the valve; maintaining an open pathway for other vessel openings of vessels that may be located in the valvular sinuses; and minimizing or reducing stress to the tissue valve leaflets. The valves of the present invention may comprise a plurality of joined leaflets with a corresponding number of commissural tabs. Generally, however, the desired valve will contain two to four leaflets and commissural tabs. Examples of other suitable valves are disclosed in U.S. patent application Ser. No. 09/772,526, issued as U.S.

Pat. No. 6,682,559 on Jan. 27, 2004, Ser. No. 09/853,463, issued as U.S. Pat. No. 6,682,558 on Jan. 27, 2004, Ser. No. 09/924,970, issued as U.S. Pat. No. 6,673,109 on Jan. 6, 2004, Ser. No. 10/121,208, issued as U.S. Pat. No. 6,719,787 on Apr. 13, 2004, Ser. No. 10/122,035, issued as U.S. Pat. No. 6,736,846 on May 18, 2004, Ser. No. 10/153,286, issued as U.S. Pat. No. 6,719,789 on Apr. 13, 2004, and Ser. No. 10/153,290, issued as U.S. Pat. No. 6,718,788 on Apr. 13, 2004, the disclosures of all of which are incorporated by reference in their entirety herein. Likewise, the systems and methods disclosed in U.S. patent application Ser. No. 10/831,770, filed Apr. 23, 2004 which published as US2005/0240200 on Oct. 27, 2005, are fully incorporated by reference herein.

As mentioned above, an open-heart valve replacement is a long tedious procedure. For implantation of a bioprosthetic valve in the aortic position, a surgeon typically opens the aorta and excises the native valve. The surgeon then inserts the prosthetic valve through the opening in the aortic wall and secures the prosthesis at the junction of the aorta and the left ventricle. The inflow annulus of the valve faces the left ventricle and, relative to the surgeon's perspective, may be termed the distal annulus, while the outflow annulus of the valve faces the aorta and may be termed the proximal annulus.

An alternative procedure for approaching the left atrium and the aortic or mitral valve is by intravascular catherization from a femoral vein through the cardiac septum, which separates the right atrium and the left atrium. Yet another alternative for approaching the left atrium and the aortic or mitral valve is by intravascular catherization from a femoral artery up through aortic valve.

Andersen et al. in U.S. Pat. No. 6,582,462, entire contents of which are incorporated herein by reference, discloses a valve prosthesis for implantation in a body channel having an inner wall, the prosthesis comprising a radially collapsible and expandable cylindrical stent, the stent including a cylindrical support means having a cylinder surface; and a collapsible and expandable valve having commissural points, the valve mounted to the stent at the commissural points, wherein the stent and valve are configured to be implanted in the body by way of catheterization. It is one aspect of the present invention to utilize a balloon expandable stent coupled with a tissue valve. An alternative embodiment in the present invention to utilizing a balloon expandable stent is to utilize a self-expandable stent. Yet another alternative embodiment of the present invention to utilizing a balloon expandable stent is to utilize a stent that may be expanded with mechanical means.

Sterman et al. in U.S. Pat. No. 6,283,127, entire contents of which are incorporated herein by reference, discloses a device system and methods facilitating intervention within the heart or great vessels without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum. The device systems and methods are particularly well adapted for heart valve repair and replacement, facilitating visualization within the patient's thoracic cavity, repair or removal of the patient's natural valve, and, if necessary, attachment of a replacement valve in the natural valve position.

Haluck in U.S. Pat. No. 6,685,724, entire contents of which are incorporated herein by reference, discloses a surgical instrument for use in performing endoscopic procedures having a handle and an elongate tubular member having a proximal end coupled with the handle for being disposed externally of the anatomical cavity and a distal end for being disposed within the anatomical cavity. The distal end further includes a pair of opposed, relatively movable jaws that form a grasping portion operable by manipulation of the handle to releasably grasp a releasable trocar. The releasable trocar has a complementarily shaped shank, a relatively sharp tip and may include a pair of blunt-edge tissue separators that project outwardly from the outer surface of the trocar.

Endoscopic and minimally invasive medical procedures, such as laparoscopy, have become widely accepted for surgery and illness diagnosis. This is due to reduced trauma to the patient and reduced hospitalization time. Other techniques exist for creating a working space within the body cavity. At the beginning of most laparoscopic cases, a small incision is made, followed by a small (about 1 cm) port in the remaining layers of the tissue wall so as to gain access to the cavity.

Hunsberger in U.S. Pat. No. 6,613,063, entire contents of which are incorporated herein by reference, discloses a trocar assembly which includes a shank having a distal end and a proximal end, and a planar piercing blade having two substantially flat faces and a cutting contour, where the piercing blade is integrally attached to the distal end of the shank. The shank tapers inwardly towards the opposed flat faces of the piercing blade.

Further, McFarlane in U.S. Pat. No. 6,478,806, entire contents of which are incorporated herein by reference, discloses a tissue penetrating instrument of the type used in the medical field and which may or may not be embodied in the form of an obturator associated with a trocar assembly, wherein the instrument includes an elongated shaft having a penetrating tip mounted on one end thereof. The penetrating tip includes a base secured to the one end of the shaft and a distal extremity spaced longitudinally outward from the base and formed into an apex which may be defined by a point or other configuration specifically structured to facilitate penetration or puncturing of bodily tissue.

Spenser et al. disclose in U.S. patent application Ser. No. 09/975,750, issued as U.S. Pat. No. 6,893,460 on May 17, 2005, Ser. No. 10/270,252, issued as U.S. Pat. No. 6,730,118 on May 4, 2004, and Ser. No. 10/637,882, which published as US2004-0039436 on Feb. 26, 2004, the entire contents of which are incorporated herein by reference, disclose and implantable prosthetic valve that comprises a support sent to be initially crimped in a narrow configuration suitable for catherization through the body duct to a target location.

Key features of any valve where sutures to hold the replacement valve into position are to be eliminated or reduced are: durability, low-pressure gradient across the valve, sufficient seal around the valve to prevent perivalvular leak, and prevent migration. Therefore, it would be desirable to provide an implantable valve that with features that aim to increase durability, reduce pressure gradient across the valve, and provide an adequate seal around the valve and prevent migration.

SUMMARY OF THE INVENTION

The present invention provides a valve prosthesis that in one embodiment comprises a support stent, comprised of a deployable construction adapted to be initially crimped in a narrow configuration suitable for catherization through the body ducts to a target location and adapted to be deployed by exerting substantially radial forces from within by means of a deployment device to a deployed state in the target location, the support stent provided with a plurality of longitudinally rigid support beams of fixed length; and a valve assembly comprising a flexible conduit having an inlet end and an outlet, made of pliant material attached to the support beams providing collapsible slack portions of the conduit at the outlet, whereby when flow is allowed to pass through the valve prosthesis device from the inlet to the outlet the valve assembly is kept in an open position whereas a reverse flow is prevented as the collapsible slack portions of the valve assembly collapse inwardly providing blockage to the reverse flow.

In another embodiment of the present invention, the support stent comprises an annular frame.

In yet another embodiment of the present invention, the support stent is made out of stainless steel.

In yet another embodiment of the present invention, said valve assembly has a tricuspid configuration.

In yet another embodiment of the present invention, said valve assembly is made from biocompatible material.

In yet another embodiment of the present invention, the valve assembly is made from pericardial tissue, or other biological tissue.

In yet another embodiment of the present invention, said valve assembly is made from biocompatible polymers.

In yet another embodiment of the present invention, the valve assembly is made from materials selected from the group consisting of polyurethane and polyethylene terphthalane.

In yet another embodiment of the present invention, the valve assembly comprises a main body made from polyethylene terphthalane and leaflets made from polyurethane.

In yet another embodiment of the present invention, said support stent is made from nickel titanium alloys.

In yet another embodiment of the present invention, the support beams are substantially equidistant and substantially parallel so as to provide anchorage for the valve assembly.

In yet another embodiment of the present invention, the support beams are provided with bores so as to allow stitching or tying of the valve assembly to the beams.

In yet another embodiment of the present invention, the support beams are not provided with bores so as to allow extra rigidity to the valve support structures.

In yet another embodiment of the present invention, the support beams are chemically adhered to the support stent.

In yet another embodiment of the present invention, said valve assembly is riveted to the support beams.

In yet another embodiment of the present invention, said beams are manufactured by injection using a mold, or by machining.

In yet another embodiment of the present invention, said valve assembly is rolled over the support stent at the inlet.

In yet another embodiment of the present invention, said valve device is manufactured using forging or dipping techniques.

In yet another embodiment of the present invention, said valve assembly leaflets are longer than needed to exactly close the outlet, thus when they are in the collapsed state substantial portions of the leaflets fall on each other creating better sealing.

In yet another embodiment of the present invention, said valve assembly is made from coils of a polymer, coated by a coating layer of same polymer.

In yet another embodiment of the present invention, said polymer is polyurethane.

In yet another embodiment of the present invention, the support stent is provided with heavy metal markers so as to enable tracking and determining the valve device position and orientation.

In yet another embodiment of the present invention, the heavy metal markers are selected from gold, platinum, iridium, tantalum, cobalt, chrome, and titanium alloys.

In yet another embodiment of the present invention, the valve assembly leaflets are provided with radio-opaque materials at the outlet so as to help tracking the valve device operation in vivo.

In yet another embodiment of the present invention, said radio-opaque material comprises gold thread.

In yet another embodiment of the present invention, the diameter of said support stent when fully deployed is in the range of from about 15 to about 33 mm.

In yet another embodiment of the present invention, the diameter of said support stent may be expanded from about 4 to about 25 mm.

In yet another embodiment of the present invention, the diameter of said support stent may be expanded from about 10 mm to about 25 mm.

In yet another embodiment of the present invention, the support beams are provided with bores and wherein the valve assembly is attached to the support beams by means of U-shaped rigid members that are fastened to the valve assembly and that are provided with extruding portions that fit into matching bores on the support beams.

In yet another embodiment of the present invention, the support beams comprise rigid support beams in the form of frame construction, and the valve assembly pliant material is inserted through a gap in the frame and a fastening rod is inserted through a pocket formed between the pliant material and the frame and holds the valve in position.

In yet another embodiment of the present invention, the main body of the valve assembly is made from coiled wire coated with coating material.

In yet another embodiment of the present invention, the coiled wire and the coating material is made from polyurethane.

In yet another embodiment of the present invention, a strengthening wire is interlaced in the valve assembly at the outlet of the conduit so as to define a fault line about which the collapsible slack portion of the valve assembly may flap.

In yet another embodiment of the present invention, the strengthening wire is made from nickel titanium alloy.

In yet another embodiment of the present invention, there is provided a valve prosthesis device suitable for implantation in body ducts, the device comprising a main conduit body having an inlet and an outlet and pliant leaflets attached at the outlet so that when a flow passes through the conduit from the inlet to the outlet the leaflets are in an open position allowing the flow to exit the outlet, and when the flow is reversed the leaflets collapse so as to block the outlet, wherein the main body is made from polyethylene terphtalate and collapsible leaflets are made from polyurethane.

In yet another embodiment of the present invention, support beams made from polyurethane are provided on the main body and wherein the leaflets are attached to the main body at the support beams.

In yet another embodiment of the present invention, said support beams are chemically adhered to the main body.

In yet another embodiment of the present invention, there is provided a valve prosthesis device suitable for implantation in body ducts, the device comprising:

A support stent, comprised of a deployable construction adapted to be initially crimped in a narrow configuration suitable for catherization through the body duct to a target location and adapted to be deployed by exerting substantially radial force from within by means of a deployment device to a deployed state in the target location, the support stent provided with a plurality of longitudinally rigid support beams of fixed length; a valve assembly comprising a flexible conduit having an inlet and an outlet, made of pliant material attached to the support beams providing collapsible slack portions of the conduit at the outlet; and substantially equidistant rigid support beams interlaced or attached to the slack portion of the valve assembly material, arranged longitudinally In yet another embodiment of the present invention, the multiple plates are adapted to move simultaneously by means of a lever and transmission.

In yet another embodiment of the present invention, there is provided a method for deploying an implantable prosthesis valve device at the natural aortic valve position at the entrance to the left ventricle of a myocardium of a patient, the method comprising the steps of: (a) providing a balloon catheter having a proximal end and a distal end, having a first and second independently inflatable portions, the first inflatable portion located at the distal end of the catheter and the second inflatable portion adjacently behind the first inflatable portion; (b) providing a guiding tool for guiding the balloon catheter in the vasculature of the patient; (c) providing a deployable implantable valve prosthesis device adapted to be mounted on the second inflatable portion of the balloon catheter; (d) guiding the balloon catheter through the patient's aorta using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position; (e) inflating the first inflatable portion of the balloon catheter so as to substantially block blood flow through the natural aortic valve and anchor the distal end of the balloon catheter in position; (f) inflating the second inflatable portion of the balloon catheter so as to deploy the implantable prosthesis valve device in position at the natural aortic valve positions; (g) deflating the first and second inflatable portions of the balloon catheter; and (h) retracting the balloon catheter and removing it from the patient's body.

In yet another embodiment of the present invention, the guiding tool compromises a guide wire.

In some further embodiments, the present invention provides a method for deploying an implantable prosthesis valve device at the natural aortic valve position at the entrance to the left ventricle of the myocardium of a patient, the method comprising the steps of: (a) providing a balloon catheter having a proximal end a distal end, having a first and second independently inflatable portions, the first inflatable portion located at the distal end of the catheter and the second inflatable portion adjacently behind the first inflatable portion; (b) providing a guiding tool for guiding the balloon catheter in the vasculature of the patient; providing a deployable implantable valve prosthesis device adapted to be mounted on the first inflatable portion of the balloon catheter, and a deployable annular stent device adapted to be mounted over the second inflatable portion of the balloon catheter, the deployable implantable valve prosthesis device and the deployable annular stent kept at a predetermined distance apart; (d) guiding the balloon catheter through the patient's aorta using the guiding tool, the valve device mounted over the first inflatable portion of the balloon catheter and the deployable annular stent mounted over the second inflatable portion of the balloon catheter, until the first inflatable portion of the balloon catheter is positioned at the natural aortic valve position; (e) inflating the second inflatable portion of the balloon catheter so that the deployable stent device is deployed within the aorta thus anchoring the deployable annular stent and the coupled valve device in position; (f) inflating the first inflatable portion of the balloon catheter so as to deploy the implantable prosthesis valve device in position at the natural aortic valve position; (g) deflating the first and second inflatable portions of the balloon catheter; and (h) retracting the balloon catheter and removing it from the patient's body.

It is one object of the valve device described in the present invention to presents a novel means of attaching a tissue valve to a support structure. The means of attaching the valve to the support structure may increase the durability of the valve, reduce the pressure gradient across the valve, provide a seal around the valve to prevent perivalvular leak, and prevent migration. The valves of the present invention may comprise a plurality of joined leaflets with a corresponding number of commissural tabs. Generally, however, the desired valve will contain two to four leaflets and commissural tabs.

In an embodiment of the present invention, the valves are similar to the valves disclosed in U.S. patent application Ser. Nos. 09/772,526, 09/853,463, 09/924,970, 10/121,208, 10/122,035, 10/153,286, 10/153,290, the disclosures of all of which are incorporated by reference in their entirety herein. The diameter of the valves described in these applications may be equal or less than the orifice diameter of the support structure of the valve.

In yet another embodiment of the present invention, the valves described in U.S. patent application Ser. Nos. 09/772,526, 09/853,463, 09/924,970, 10/121,208, 10/122,035, 10/153,286, 10/153,290, the valves are sized such that the effective valve diameter is 1-5 mm less than the diameter of the orifice of the support structures of the valve. This size will help prevent the valve leaflets from hitting the support structure.

In yet another embodiment of the present invention, the valves are made of equine pericardium.

In yet another embodiment of the present invention, a cuff (e.g. cloth) portion of the valve assembly is wrapped around the support stent at the inlet. This may enhance stability of the stent, but further, the cuff portion described in the current invention may be used for attaching sutures. Most importantly, the cuff portion of the present invention is intended to reduce perivalvular leak around the valve. Using such a cuff to create a seal between the valve structure and the aorta prevents perivalvular leak and is especially important in patients whose annulus (or landing zone for the valve) is calcified or irregular. The cuff may also prevent migration of the valve as the friction between the valve device and the surrounding is increased. Utilizing a cloth cuff may also induce tissue ingrowth. The cloth may initially clot when it is exposed to blood. The cloth may further induce endothelial and fibroblast, and hence tissue ingrowth into the cloth cuff.

In yet another embodiment of the present invention the cloth cuff creates a step between a thin cloth covering around the inlet portion of the valve assembly that moves up to a much thicker cloth cuff slightly further downstream in the assembly. Such a "lip" or "step" may help position and secure the valve prosthesis at the correct position.

In yet other embodiments of the present invention, the scalloped inflow edge described in U.S. application Ser. Nos. 09/772,526, 09/853,463, 09/924,970, 10/121,208, 10/122,035, 10/153,286, 10/153,290, is sutured onto the cuff portion of the valve assembly described above. Another use of the cuff is thus to allow a valve with a scalloped inflow edge to be attached to a non-scalloped stent.

In yet other embodiments of the present invention, the support beams of the stent are extended at the inflow portion to accommodate the length of longer valves such as the ones described in U.S. application Ser. Nos. 09/772,526, 09/853,463, 09/924,970, 10/121,208, 10/122,035, 10/153,286, 10/153,290.

In yet another embodiment of the present invention, the support beams form eyelets at the outflow edge that the tabs of the valves described in U.S. application Ser. Nos. 09/772,526, 09/853,463, 09/924,970, 10/121,208, 10/122,035, 10/153,286, 10/153,290 may be attached to. The valve tabs may be sutured to the eyelets around the perimeter of the eyelet. Such a configuration helps distribute the stress around the tabs and reduce the wear and tear on the commissural posts of the valve.

In yet another embodiment of the present invention, the support beam eyelets described above are covered with cloth. Covering the eyelets and tabs with cloth may help induce tissue ingrowth.

In yet another embodiment of the present invention, the valve device is made such that it cannot be crimped down beyond the diameter of a typical femoral artery or a femoral vein (where the catheter can typically be no more than 8 mm). In other words, the valve device is made such that it cannot be implanted through the femoral artery or femoral vein.

In yet another embodiment of the present invention, the valve device is crimped just after it has been manufactured, and shipped from the manufacturer in the crimped state to the hospital or where it is to be implanted.

In yet another embodiment of the present invention, the stent is made out of a memory shaped metal or a memory shaped polymer.

In yet another embodiment of the present invention, the stent of the valve device is made to be balloon expandable.

In yet another embodiment of the present invention, the stent of the valve device is made to be self-expandable.

The present invention provides systems and devices for the replacement of physiological valves. In one embodiment of the present invention, the replacement valve assemblies are adapted to fit substantially within the valve sinuses. Because the devices and procedures provided by the present invention eliminate or reduce the need for suturing, time spent in surgery is significantly decreased, and the risks associated with surgery are minimized. Further, the devices of the present invention are suitable for delivery by cannula or catheter.

In yet another embodiment of the present invention, the stent of the valve device is made such as to expand into the sinus regions during balloon expansion.

In yet another embodiment of the present invention, the stent of the valve devices is made such as to expand into the sinus region during self-expansion.

In one embodiment of the present invention a valve anchoring structure is provided that is dimensioned to be placed substantially within the valve sinus. In this embodiment, the valve anchoring structure extends substantially across the length of the valve sinus region.

In another embodiment of the present invention a valve assembly is provided, comprising a valve and anchoring structure, in which the valve comprises a body having a proximal end and a distal end, an inlet at the proximal end, and an outlet at the distal end. The inlet comprises an inflow annulus, with either a scalloped or straight edge. The outlet comprises a plurality of tabs that are supported by the anchoring means at the distal end. In an embodiment of the invention, the plurality of tabs is spaced evenly around the circumference of the valve.

In yet another embodiment of the present invention, a valve assembly is provided in which there is minimal or no contact between the valve and anchoring structure.

In still another embodiment of the present invention, a valve assembly is provided in which the valve is capable of achieving full opening and full closure without contacting the anchoring structure.

In yet another embodiment of the present invention, a valve assembly is provided in which the vertical components of the anchoring structure are limited to the commissural posts between sinus cavities, thereby minimizing contact between mechanical components and fluid, as well as providing flow to vessels located in the valve sinus.

In still another embodiment of the present invention, a valve is provided that firmly attaches to the valve sinus, obviating the need for suturing to secure the valve placement.

In a further embodiment of the present invention, a valve assembly is provided in which the anchoring structure may be collapsed to at least fifty percent of its maximum diameter.

In still a further embodiment of the present invention, an expansion and contraction device is provided to facilitate implantation of the valve and anchoring structure.

In another embodiment, the present invention provides adhesive means for securing the valve assembly in a valve sinus.

In yet another embodiment of the present invention, a valve sizing apparatus is provided for the noninvasive determination of native valve size.

DESCRIPTION OF DRAWINGS

To better understand the present invention and appreciate its practical applications, the following Figures are provided and referenced hereafter. It should be noted that the Figures are given as examples only and in no way limit the scope of the invention.

DETAILED DESCRIPTION

Figure 1:
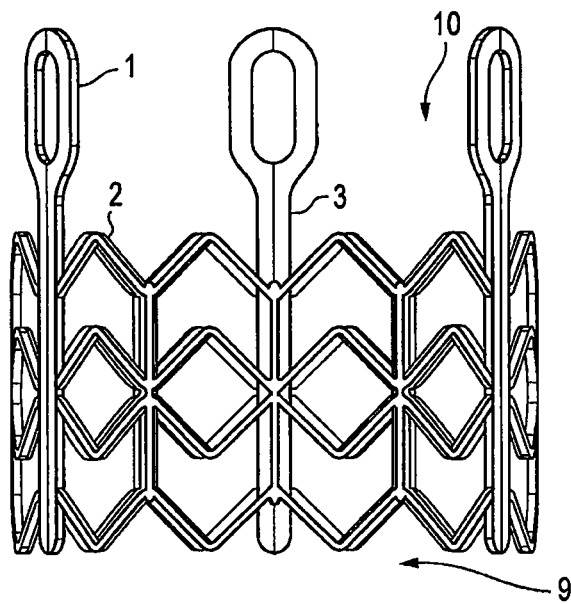
FIG. 1 shows the valve structure, stent, or frame seen from the side.

A main aspect of the present invention is the introduction of several novel designs for an implantable prosthesis valve. Another aspect of the present invention is the disclosure of several manufacture methods for the manufacturing of implantable prosthesis valves in accordance with the present invention. A further aspect of the present invention is the provision of novel deployment and positioning techniques suitable for the valve of the present invention.

Basically the implantable prosthetic valve of the present invention comprises a leafed-valve assembly, preferably tricuspid but not limited to tricuspid valves only, consisting of a conduit having an inlet end and an outlet, made of pliant material arranged so as to present collapsible walls at the outlet. The valve assembly is mounted on a support structure such as a stent adapted to be positioned at a target location within the body duct and deploy the valve assembly by the use of deploying means, such as a balloon catheter or similar devices. In embodiments suitable for safe and convenient percutaneous positioning and deployment the annular frame is able to be posed in two positions, a crimped position where the conduit passage cross-section presented is small so as to permit advancing the device towards its target location, and a deployed position where the frame is radial extended by forces exerted from within (by deploying means) so as to provide support against the body duct wall, secure the valve in position and open itself so as to allow flow through the conduit.

The valve assembly can be made from biological matter, such as a natural tissue, pericardial tissue or other biological tissue. Alternatively, the valve assembly may be made form biocompatible polymers or similar materials. Homograph biological valves need occasional replacement (usually within 5 to 14 years) and this is a consideration the surgeon must take into account, when selecting the proper valve implant according to the patient type. Metal mechanical valves, which have better durability qualities, carry the associated risk of long-term anticoagulation treatment.

The frame can be made from shape memory alloys such as nickel titanium (nickel titanium shape memory alloys, or NiTi, as marketed, for example, under the brand name Nitinol), or other biocompatible metals. The percutaneously implantable embodiment of the implantable valve of the present invention has to be suitable for crimping into a narrow configuration for positioning and expandable to a wider, deployed configuration so as to anchor in position in the desired target location.

The support stent is preferably annular, but may be provided in other shapes too, depending on the cross-section shape of the desired target location passage.

Manufacturing of the implantable prosthetic valve of the present invention can be done in various methods, for example, by dipping, injection, electrospinning, rotation, ironing, or pressing.

The attachment of the valve assembly to the support stent can be accomplished in several ways, such as by sewing it to several anchoring points on the support stent, or riveting it, pinning it, or adhering it, to provide a valve assembly that is cast or molded over the support stent, or use any other suitable way of attachment.

To prevent leakage from the inlet it is optionally possible to roll up some slack wall of the inlet over the edge of the frame so as to present rolled-up sleeve-like portion at the inlet.

Furthermore, floating supports may be added to enhance the stability of the device and prevent it from turning inside out.

An important aspect of certain embodiments of the present invention is the provision of rigid support beams incorporated with the support stent that retains its longitudinal dimension while the entire support stent may be longitudinally or laterally extended.

The aforementioned embodiments as well as other embodiments, manufacturing methods, different designs and different types of devices are discussed and explained below with reference to the accompanying drawings. Note that the drawings are only given for the purpose of understanding the present invention and presenting some preferred embodiments of the present invention, but this does in no way limit the scope of the present invention as defined in the appended claims.

Reference is now made to FIG. 1, which illustrates a valve support structure or frame shown in a deployed position. The frame has an inlet 9 and an outlet side 10. The frame is arranged in a net-like frame designed to be crimped evenly so as to present a narrow configuration and be radially deployable so as to extend to occupy the passage at the target location for implantation in a body duct. Support beams 3 are provided on annular support stent 2 to provide rigidity and anchorage to the valve. Support beams 3 may be provided with bores to provide attachment for a valve. In the current Figure, the support beams are solid as to provide extra rigidity to the stent. The support beams 3 transition into oval eyelets 1 at the outflow edge.

Figure 2:
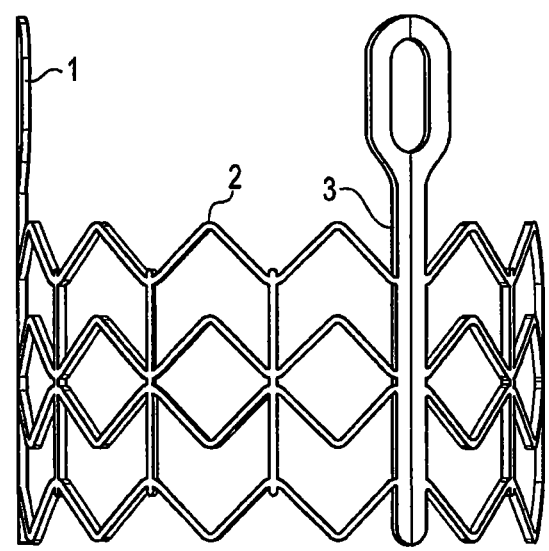
FIG. 2 shows the valve structure, stent, or frame seen from the side.
Figure 3:
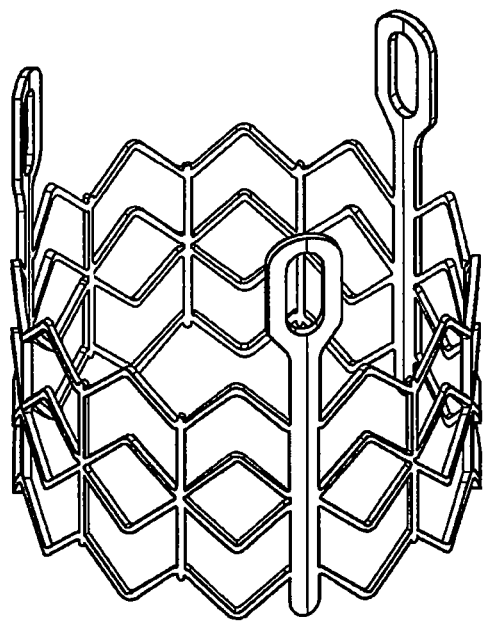
FIG. 3 shows the valve structure, stent, or frame seen from an isometric view.
Figure 4:
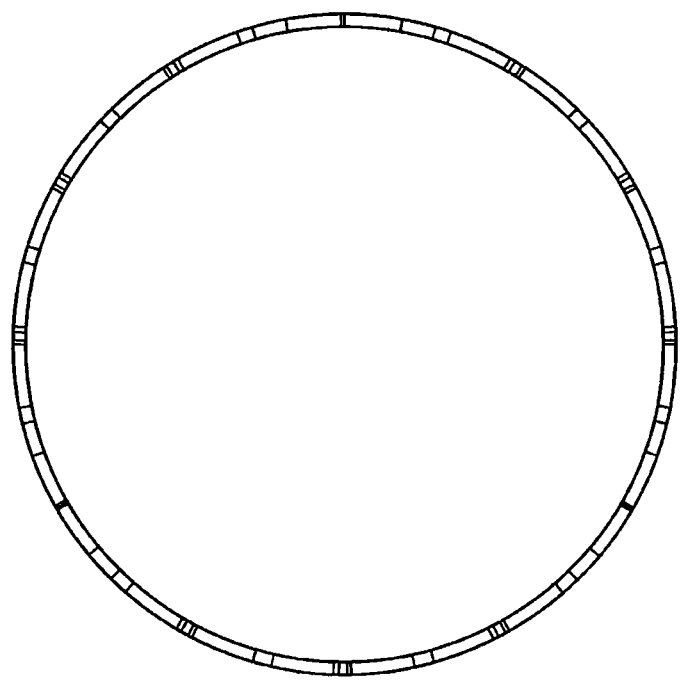
FIG. 4 shows the valve structure, stent, or frame seen from the top (i.e. at the outflow side).

FIGS. 2-4 show the same frame seen in FIG. 1 from different perspectives.

Note that the entire valve structure is adapted to be radially crimped and radially expanded, and this lends to provide ease of navigation through narrow passages in the vasculature during positioning of the device and adequate deployment on the final location. This is made possible by the provision of a collapsible support stent structure. However, the support beams always maintain the same length. Because the support beams maintain the same length, the distance between the inflow edge and the tab attachments of the valve are maintained during crimping and expansion. This allows the valve to function properly. In prior art implantable valve devices the entire support structure changes its dimensions from its initial first crimped position and final deployed position, and this means that in the attachment of the valve assembly to the support structure one must take into consideration these dimension changes and leave slack material so that upon deployment of the device the valve assembly does not tear or deform. In the valve device of the present invention there is no relative movement between the valve assembly and the support beams (along the longitudinal central axis of the device). As a result, the valve device of the present invention acquires greater durability and is capable of withstanding the harsh conditions prevailing within the heart. The novel design of the valve device of the present invention leads to longitudinal strength and rigidity whereas its collapsible support structure results in radial flexibility.

Figure 5:
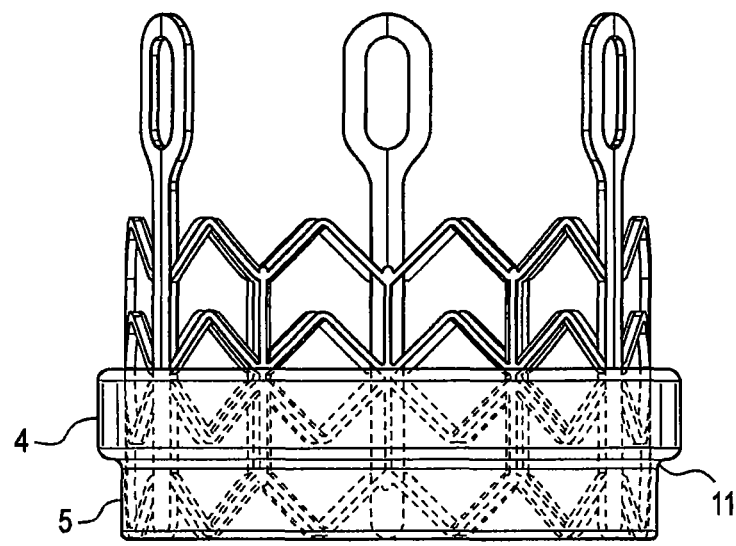
FIG. 5 shows the frame with a cloth cover around the inflow edge.

FIG. 5 shows the cloth cuff (4 and 5) at the inflow edge of the stent. The cloth cuff has a circular inlet end and a circular outlet end. The cloth cuff may consist of a thin cloth cuff 5 and a thicker cloth cuff 4 and thus create a lip 11 at the intersection between these two cuffs. This "lip" or "step" may help position and secure the valve prosthesis at the correct position. It may, for example, help hold the valve prosthesis at the inflow annulus when placed in the aortic position.

Figure 6:
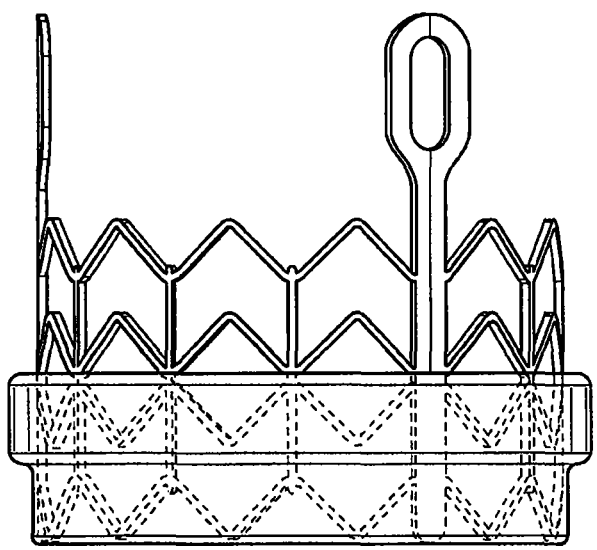
FIG. 6 shows the frame with a cloth cover around the inflow edge.
Figure 7:
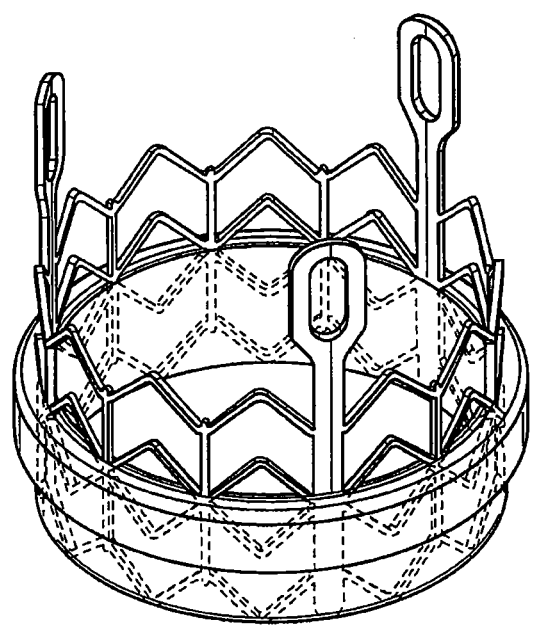
FIG. 7 shows the frame with cloth cover around the inflow edge.
Figure 8:
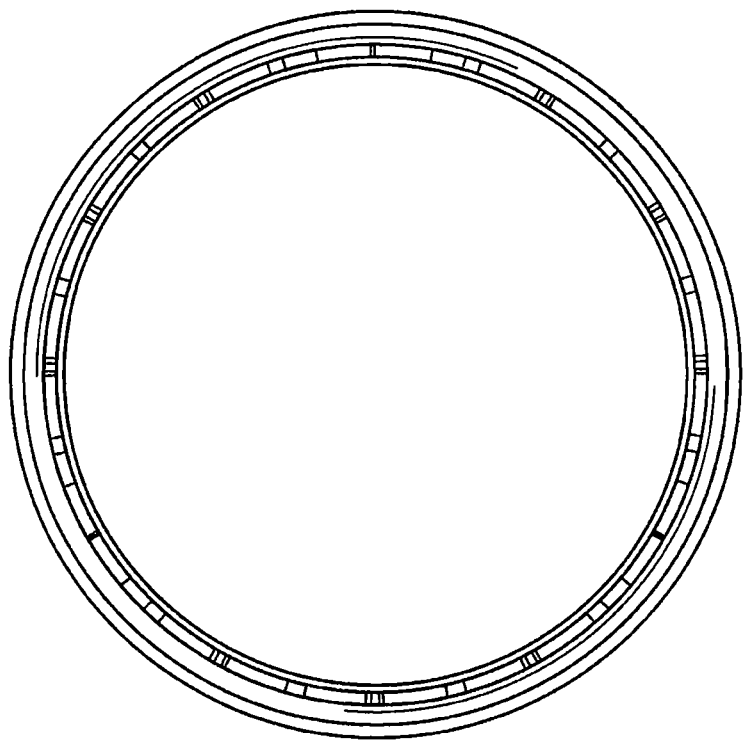
FIG. 8 shows the frame with cloth cover around the inflow edge.

FIGS. 6-8 show the same frame and tissue cuffs seen in FIG. 5 from different perspectives.

Figure 9:
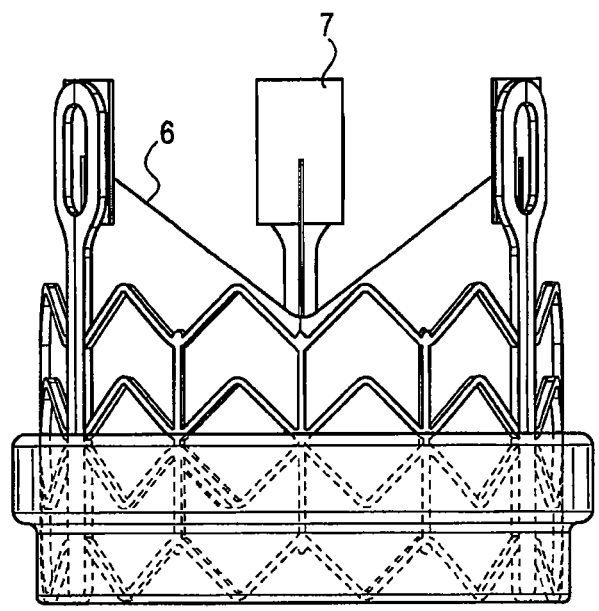
FIG. 9 shows the frame with cloth cover around the inflow edge. The valve is also attached in this figure. The tabs of the valve are aligned with the eyelets of the frame.

FIG. 9 shows one of the valves 6 disclosed in U.S. patent application Ser. Nos. 09/772,526, 09/853,463, 09/924,970, 10/121,208, 10/122,035, 10/153,286, 10/153,290. The tabs 7 of the valve are aligned with the eyelets 1 of the support beams. The overall size of the eyelets 1 match the size of the tabs 7. The valve 6 is attached at the inflow side of the frame 9 and is sutured to the cloth cuff 5 and 4.

Figure 10:
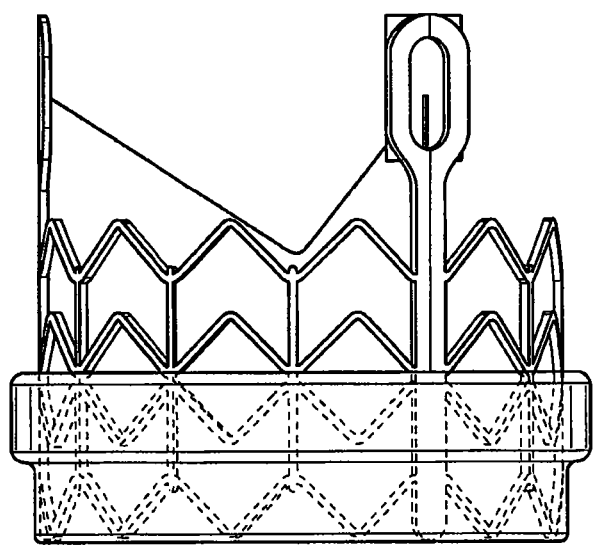
FIG. 10 shows the frame with cloth cover around the inflow edge. The valve is also attached in this figure. The tabs of the valve are aligned with the eyelets of the frame.
Figure 11:
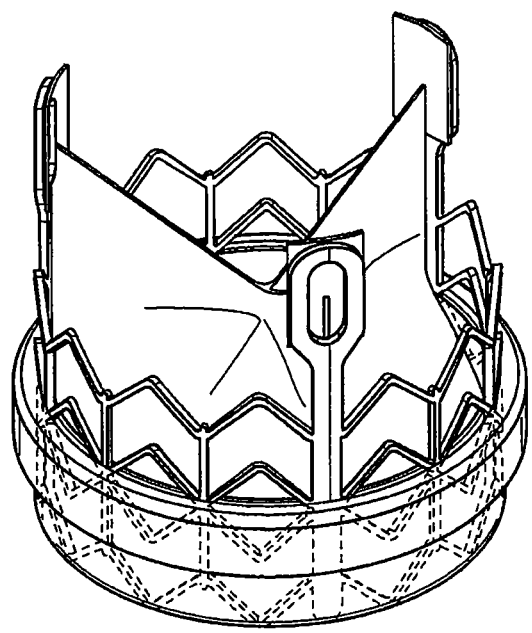
FIG. 11 shows the frame with cloth cover around the inflow edge. The valve is also attached in this figure. The tabs of the valve are aligned with the eyelets of the frame.
Figure 12:
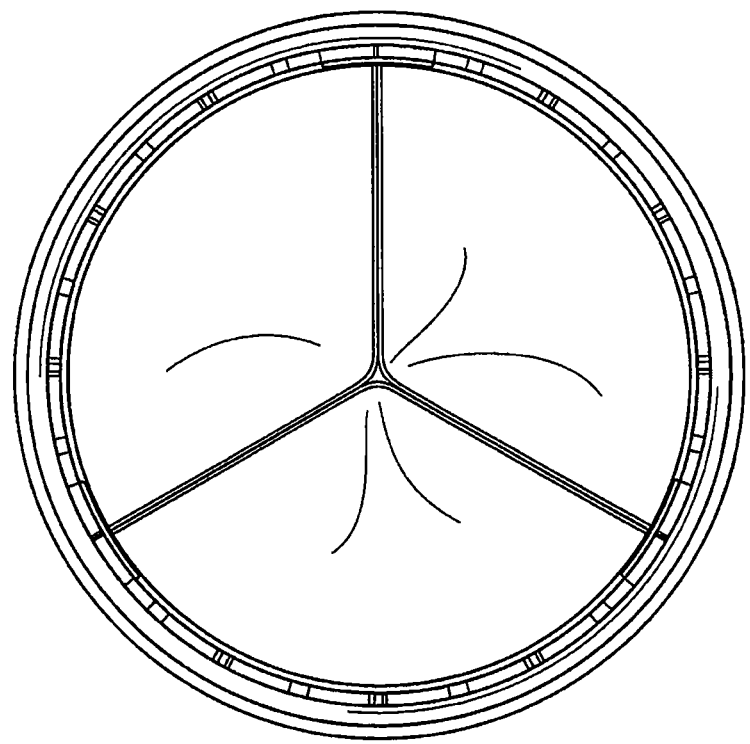
FIG. 12 shows the frame with cloth cover around the inflow edge. The valve is also attached in this figure. The tabs of the valve are aligned with the eyelets of the frame.

FIGS. 10-12 show the same valve assembly seen in FIG. 9 from different perspectives.

Figure 13:
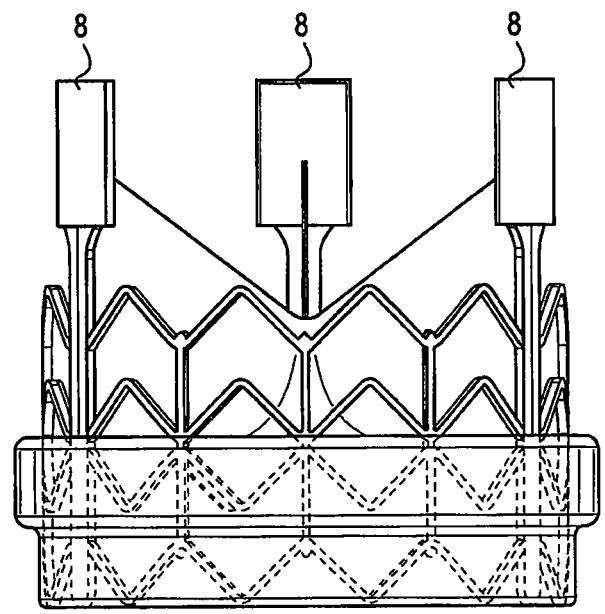
FIG. 13 shows the frame with cloth cover around the inflow edge. The valve is also attached in this figure. The tabs of the valve are aligned with the eyelets of the frame. Cloth has been added and keeps the valve tabs attached to the frame eyelets.

FIG. 13 shows the complete valve assembly. In this Figure, the tabs 7 and the eyelets 1 have been covered with cloth 8. Covering the tabs 7 with a cloth cuff may induce tissue ingrowth. The cloth may initially clot when it is exposed to blood. The cloth may further induce endothelial and fibroblast, and hence tissue ingrowth. Inducing tissue ingrowth will reduce the loads imposed on the stent. Covering the tabs 7 and the eyelets 1 with cloth 8 in this manner will also help distribute the load seen by the commissural posts across the entire tab, hence reducing wear and tear on the commissural posts of the valve.

Figure 14:
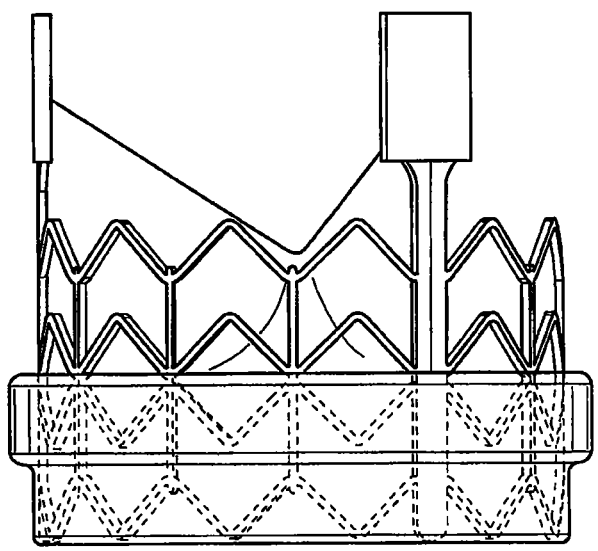
FIG. 14 shows the frame with cloth cover around the inflow edge. The valve is also attached in this figure. The tabs of the valve are aligned with the eyelets of the frame. Cloth has been added and keeps the valve tabs attached to the frame eyelets.
Figure 15:
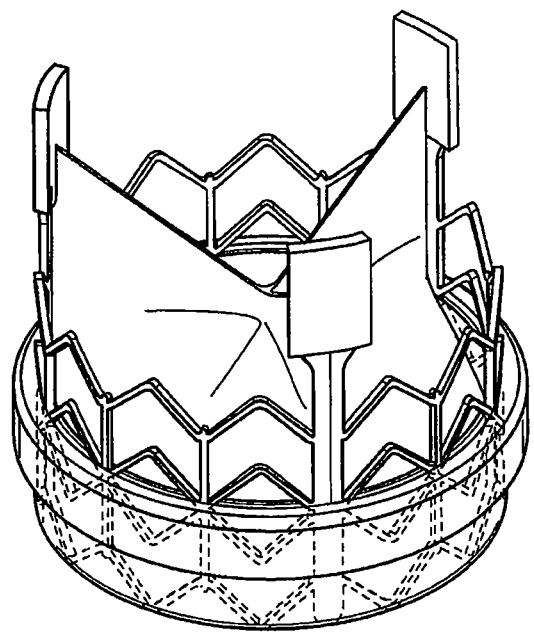
FIG. 15 shows the frame with cloth cover around the inflow edge. The valve is also attached in this figure. The tabs of the valve are aligned with the eyelets of the frame. Cloth has been added and keeps the valve tabs attached to the frame eyelets.
Figure 16:
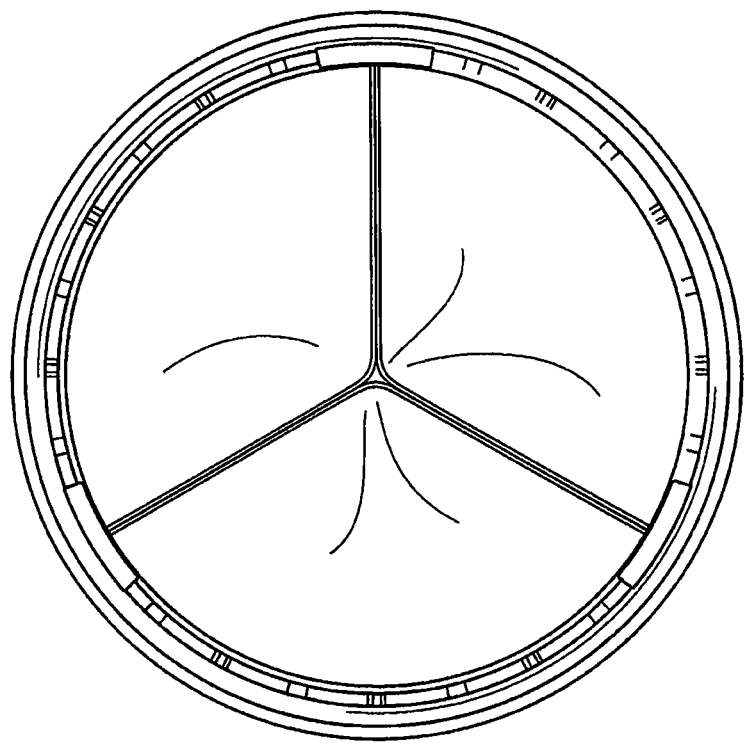
FIG. 16 shows the frame with cloth cover around the inflow edge. The valve is also attached in this figure. The tabs of the valve are aligned with the eyelets of the frame. Cloth has been added and keeps the valve tabs attached to the frame eyelets.

FIGS. 14-16 show the same valve assembly seen in FIG. 13 from different perspectives.

Figure 17:
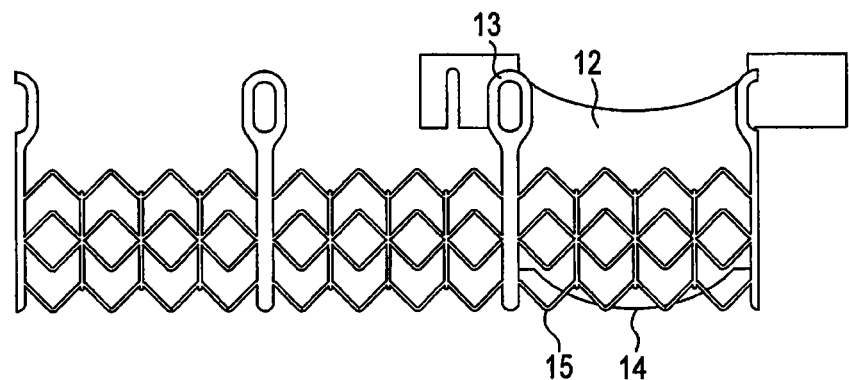
FIG. 17 shows one of the leaflets described in U.S. application Ser. Nos. 09/772,526, 09/853,463, 09/924,970, 10/121,208, 10/122,035, 10/153,286, 10/153,290 and shows how this is aligned with the frame and frame eyelets. The cloth cuff around the inflow edge has been removed for clarity.

FIG. 17 shows one of the leaflets 12 described in U.S. application Ser. Nos. 09/772,526, 09/853,463, 09/924,970, 10/121,208, 10/122,035, 10/153,286, 10/153,290 and shows how this is aligned with the frame 15 and frame eyelets 13. The cloth cuff around the inflow edge has been removed for clarity. Another embodiment that is evident in FIG. 17 is how the scalloped edge of the leaflet 14 is positioned relative to the inlet of the stent 15.

Figure 18:
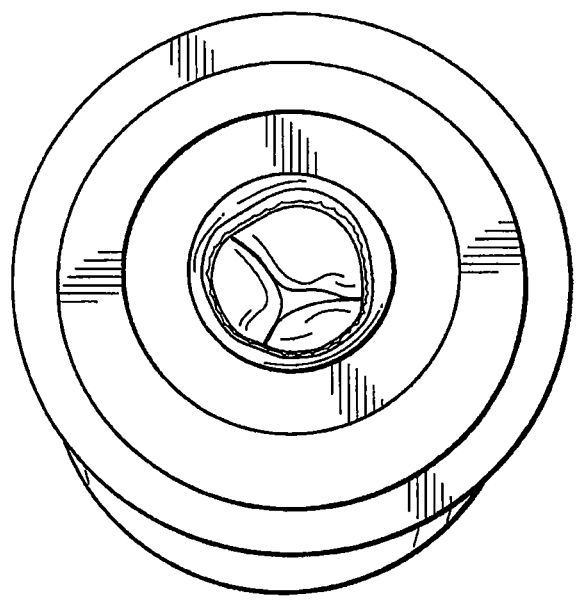
FIG. 18 shows the outflow side of a prototype valve prosthesis.
Figure 19:
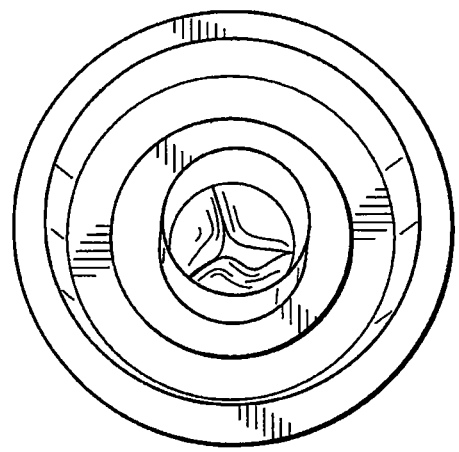
FIG. 19 shows the inflow side of a prototype valve prosthesis.
Figure 20:
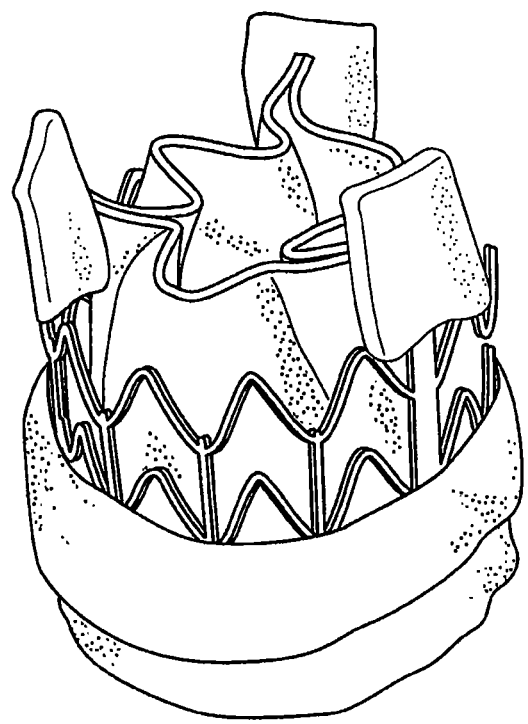
FIG. 20 shows a side view of a prototype valve prosthesis.

FIGS. 18-20 show pictures of a prototype valve that has been assembled.

Figure 21:
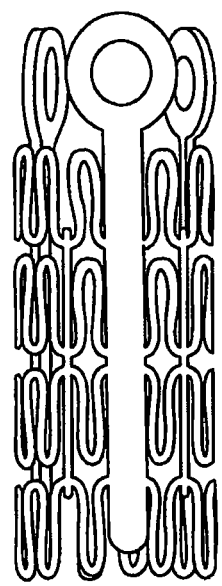
FIG. 21 shows the stent of the valve assembly crimped down to 7.5 mm

FIG. 21 shows a picture of a stent crimped to 7.5 mm.

Figure 22A:
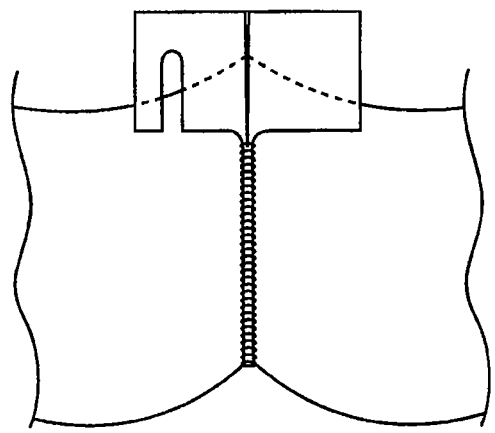
FIG. 22 shows the assembly of the valve tab to frame eyelet
Figure 22B:
Figure 22C:

FIG. 22 shows the assembly of the valve tab to frame eyelet.

Figure 23A:
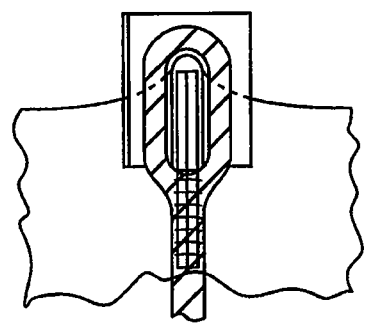
FIG. 23 shows final cloth covering of tab/eyelet assembly.
Figure 23B:
Figure 23C:
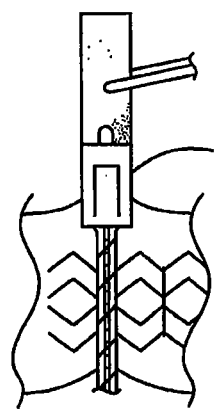

FIG. 23 shows the final cloth covering of tab/eyelet assembly.

A typical size of an aortic prosthesis valve is from about 19 to about 31 mm in diameter. A maximal size of a catheter inserted into the femoral artery should be no more than 8 mm in diameter. The present invention introduces a device, which has the ability to change its diameter from about 4 mm to about 33 mm. Artificial valves are not new; however, artificial valves in accordance with the present invention posses the ability to change shape and size for the purpose of delivery and as such are novel. These newly designed valves require new manufacturing methods and technical inventions and improvements, some of which were described herein.

As described before, one embodiment of the present invention is to make it impossible for the stent to be crimped down below the size of the femoral artery or vein. In other words, one may create mechanical stops or add tissue or cloth in a manner as to prevent the stent from being capable of being crimped further down than beyond the size of the femoral artery or vein. In this manner, the stent is made such that it intentionally cannot be used through a femoral vein or femoral artery access. Creating such size constraints on the valve assembly may make it possible to create a sturdier device for prolonging the longevity of the valve assembly. Such a device could be implanted through the apex of the heart, as described in details in a U.S. patent application no. 10/831,770 submitted Apr. 23, 2004 entitled "Method and System for Cardiac Valve Delivery". An early version of this document is submitted at the same time as the current provisional. No application number exists at this point. The application is appended to this provisional patent application, and is hereby included in this application in its entirety.

As mentioned earlier, the material of which the valve is made from can be either biological or artificial. In any case new technologies are needed to create such a valve.

To attach the valve to the body, the blood vessels determine the size during delivery, and the requirements for it to work efficiently, there is a need to mount it on a collapsible construction which can be crimped to a small size, be expanded to a larger size, and be strong enough to act as a support for the valve function. This construction, which is in somewhat similar to a large "stent", can be made of different materials such as Nitinol, biocompatible stainless steel, polymeric material or a combination of all. Special requirement for the stent are a subject of some of the embodiments discussed herein.

The mounting of the valve onto a collapsible stent is a new field of problems. New solutions to this problem are described herein.

Another major aspect of the design of the valve of the present invention is the attachment to the body.

Yet another major aspect of the valve apparatus is the attachment of the valve to the frame.

In the traditional procedure the valve is sutured in place by a complicated suturing procedure. In the case of the percutaneous procedure there is no direct access to the implantation site therefore different attachment techniques are needed.

Another new problem that is dealt herein is the delivery procedure, which is new and unique. Positioning of the device in the body in an accurate location and orientation requires special marking and measuring methods of the device and surgical site as was disclosed herein.

Artificial polymer valves require special treatment and special conditions when kept on a shelf, as well as a special sterilization procedure. One of the consequences of the shelf treatment is the need to crimp the valve during the implantation procedure. A series of devices and inventions to allow the crimping procedure are disclosed herein.

It should be clear that the description of the embodiments and attached Figures set forth in this specification serves only for a better understanding of the invention, without limiting its scope as covered by the following claims.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed is:

1. A prosthetic valve assembly comprising:
a support structure having an inlet end and an outlet end, wherein the support structure includes a plurality of longitudinally rigid support beams, said support structure configured to be radially collapsible and expandable;
a valve comprising a pliant material having an inlet and an outlet, wherein said pliant material has a plurality of tabs at said outlet, and wherein said plurality of tabs are attached to said support beams at said outlet end of said support structure; and
a cuff operably attached to an outer surface of said support structure at said inlet of said support structure, wherein said cuff is disposed radially outside of said support beams, wherein said cuff has a radial lip configured to facilitate positioning and securing said valve assembly in a body lumen, wherein said cuff comprises a first cylindrical portion and a second cylindrical portion, said first cylindrical portion having greater thickness than said second cylindrical portion, wherein the first cylindrical portion is disposed downstream of the second cylindrical portion, and wherein said radial lip is defined by an interface of said first cylindrical portion and said second cylindrical portion.

2. The prosthetic valve assembly of claim 1 wherein said cuff comprises a material configured to facilitate tissue ingrowth.

3. The prosthetic valve assembly of claim 1 wherein said cuff comprises a cloth material.

4. The prosthetic valve assembly of claim 1 wherein said plurality of tabs are commissural tabs that are operably attached to eyelets on said outlet end of at least two of said plurality of longitudinally rigid support beams.

5. The prosthetic valve assembly of claim 4 wherein said plurality of tabs are sutured to said eyelets around a perimeter of each of said eyelets.

6. The prosthetic valve assembly of claim 1 further comprising cloth portions covering said plurality of tabs and said outlet end of said support structure.

7. The prosthetic valve assembly of claim 1 wherein said support structure comprises a material selected from the group consisting of memory shaped metals, memory shaped polymers, biocompatible stainless steel and polymeric material.

8. The prosthetic valve assembly of claim 7 wherein said support structure comprises polyethylene terphthalene.

9. The prosthetic valve assembly of claim 1 wherein said valve comprises at least two leaflets having tabs integrally formed thereon.

10. The prosthetic valve assembly of claim 9 wherein said leaflets comprise a material selected from the group consisting of natural tissue and biocompatible materials.

11. The prosthetic valve assembly of claim 10 wherein said natural tissue is pericardial tissue.

12. The prosthetic valve assembly of claim 10 wherein said biocompatible material is polyurethane.

13. The prosthetic valve assembly of claim 1 wherein said support structure is configured to be radially collapsible to a diameter of 4-25 mm while retaining a fixed longitudinal length.

14. The prosthetic valve assembly of claim 1 wherein said support structure is configured to be radially expandable to a diameter of 10-33 mm while retaining a fixed longitudinal length.

15. The prosthetic valve assembly of claim 1 wherein said support structure comprises an annular frame and said valve has a generally tubular shape, said valve having an outer diameter that is 1-5 mm smaller than an inner diameter of said support structure.

16. The prosthetic valve assembly of claim 1 wherein said valve comprises a tricuspid configuration.

17. The prosthetic valve assembly of claim 1 wherein said plurality of longitudinally rigid support beams are spaced equidistantly around said support structure.

18. The prosthetic valve assembly of claim 17 wherein said plurality of longitudinally rigid support beams are positioned parallel to one another.

19. The prosthetic valve assembly of claim 1 wherein said valve is attached to said cuff.

20. The prosthetic valve assembly of claim 1 wherein said plurality of longitudinally rigid support beams are attached to said support structure with rivets or an adhesive.

21. The prosthetic valve assembly of claim 1 wherein said plurality of longitudinally rigid support beams are integrally formed with said support structure.

22. The prosthetic valve assembly of claim 1 wherein said support structure has at least one marker configured to track and determine position and orientation of said prosthetic valve assembly.

23. The prosthetic valve assembly of claim 22 wherein said at least one marker comprises a metal selected from the group consisting of gold, platinum, iridium, tantalum, cobalt, chrome and titanium alloys.

24. The prosthetic valve assembly of claim 1 wherein said valve has a radio-opaque material at said outlet, said radio-opaque material configured to facilitate in vivo tracking of said valve assembly.

25. The prosthetic valve assembly of claim 24 wherein said radio-opaque material comprises gold thread.

26. The prosthetic valve assembly of claim 1 wherein said valve has collapsible slack portions at said outlet, said collapsible slack portions configured to allow blood to pass through said prosthetic valve assembly when flowing from said inlet end to said outlet thereby holding said collapsible slack portions in an open position, said collapsible slack portions further configured to prevent reverse blood flow by collapsing inwardly and maintaining said collapsible slack portions in a closed position.

27. The prosthetic valve assembly of claim 26 further comprising a strengthening wire disposed along said outlet of said valve and configured to support said collapsible slack portions.

28. The prosthetic valve assembly of claim 27 wherein said strengthening wire comprises nickel titanium.

29. A method for implanting a prosthetic valve assembly comprising:
(a) providing a catheter having a proximal end and a distal end;
(b) mounting said prosthetic valve assembly on said distal end, said prosthetic valve assembly comprising
(i) a support structure having an inlet end, an outlet end and a plurality of longitudinally rigid support beams disposed thereon, said support structure configured to be radially collapsible and expandable while retaining a fixed longitudinal length;
(ii) a valve comprised of a pliant material having an inlet end and an outlet, said pliant material having a plurality of tabs at said outlet configured to be operably attached to said support beams at said outlet end of said support structure; and
(iii) a cuff operably attached to an outer surface of said support structure at said inlet of said support structure, wherein said cuff is disposed radially outside of said support beams, wherein said cuff has a radial lip configured to facilitate positioning and securing said valve assembly in a body lumen, wherein said cuff comprises a first cylindrical portion and a second cylindrical portion, said first cylindrical portion having greater thickness than said second cylindrical portion, wherein the first cylindrical portion is disposed downstream of the second cylindrical portion, and wherein said radial lip is defined by an interface of said first cylindrical portion and said second cylindrical portion;
(c) guiding said catheter through said body lumen to a target site with a guiding tool;
(d) deploying said prosthetic valve assembly at said target location; and
(e) retracting said catheter.

30. The method of claim 29 wherein said guiding tool comprises a guidewire.

31. The method of claim 29 wherein said cuff is comprised of a material configured to facilitate tissue ingrowth.

32. The method of claim 29 wherein said cuff comprises a cloth material.

33. The method of claim 29 wherein said plurality of tabs are commissural tabs that are operably attached to eyelets on said outlet end of at least two of said plurality of longitudinally rigid support beams.

34. The method of claim 33 further comprising suturing said plurality of tabs to said eyelets around a perimeter of each of said eyelets.

35. The method of claim 29 further comprising covering said plurality of tabs and said outlet end of said support structure with cloth portions for promoting tissue ingrowth.

36. The method of claim 29 wherein said support structure comprises a material selected from the group consisting of memory shaped metals, memory shaped polymers, biocompatible stainless steel and polymeric material.

37. The method of claim 36 wherein said support structure comprises polyethylene terphthalene.

38. The method of claim 29 wherein said valve comprises at least two leaflets having tabs integrally formed thereon.

39. The method of claim 38 wherein said leaflets comprise a material selected from the group consisting of natural tissue and biocompatible materials.

40. The method of claim 39 wherein said natural tissue is pericardial tissue.

41. The method of claim 39 wherein said biocompatible material is polyurethane.

42. The method of claim 29 wherein the step for guiding said catheter through said body lumen to a target site with said guiding tool further comprises radially collapsing said prosthetic valve assembly to a diameter of 4-25 mm while maintaining a fixed longitudinal length of said prosthetic valve assembly.

43. The method of claim 29 wherein the step for deploying said prosthetic valve assembly at said target location further comprises radially expanding said prosthetic valve assembly to a diameter of 10-33 mm while retaining a fixed longitudinal length of said prosthetic valve assembly.

44. The method of claim 29 further comprising sizing said valve and said support structure to allow said valve to fully open and close without contacting said support structure.

45. The method of claim 29 wherein said valve comprises a tricuspid configuration.

46. The method of claim 29 wherein said plurality of longitudinally rigid support beams are spaced equidistantly around said support structure.

47. The method of claim 46 wherein said plurality of longitudinally rigid support beams are positioned parallel to one another.

48. The method of claim 29 further comprising adhering said plurality of longitudinally rigid support beams to said support structure with an adhesive.

49. The method of claim 29 further comprising attaching said plurality of longitudinally rigid support beams to said support structure with rivets.

50. The method of claim 29 further comprising integrally forming said plurality of longitudinally rigid support beams with said support structure.

51. The method of claim 29 further comprising providing at least one marker configured to track and determine position and orientation of said prosthetic valve assembly.

52. The method of claim 51 wherein said at least one marker comprises a metal selected from the group consisting of gold, platinum, iridium, tantalum, cobalt, chrome and titanium alloys.

53. The method of claim 29 wherein said valve has a radio-opaque material at said outlet for facilitating in vivo tracking of said valve assembly.

54. The method of claim 53 wherein said radio-opaque material comprises gold thread.

55. The method of claim 29 further comprising attaching said valve to said support structure with at least one U-shaped rigid member wherein said plurality of longitudinally rigid support beams have bores configured to receive extruded portions of at least one U-shaped rigid member.

56. The method of claim 29 wherein said plurality of longitudinally rigid support beams comprise a frame construction having a plurality of gaps therewithin, and further wherein said pliant material is inserted in at least one of said plurality of gaps.

57. The method of claim 56 further comprising a fastening rod insertable through a pocket formed between said pliant material and said frame construction.

58. The method of claim 29 wherein said support structure comprises a coiled wire coated with a coating material.

59. The method of claim 58 wherein said coating material comprises polyurethane.

60. The method of claim 29 wherein said valve has collapsible slack portions at said outlet, said collapsible portions configured to allow blood to pass through said prosthetic valve assembly when flowing from said inlet end to said outlet thereby holding said collapsible portions in an open position, said collapsible portions further configured to prevent reverse blood flow by collapsing inwardly and maintaining said collapsible portions in a closed position.

61. The method of claim 60 further comprising a strengthening wire disposed along said outlet of said valve for supporting said collapsible portions.

62. The method of claim 61 wherein said strengthening wire comprises nickel titanium.

63. The method of claim 29 further comprising at least one inflatable portion on said distal end of said catheter, said inflatable portion configured to radially expand said prosthetic valve assembly for deploying said prosthetic valve assembly at said target location.

64. The method of claim 29 wherein said support structure is radially self expanding for deploying said prosthetic valve assembly at said target location.

\* \* \* \* \*